United States Patent [19]
Sih

[11] 4,296,256
[45] Oct. 20, 1981

[54] 2-DECARBOXY-2-HYDROXYMETHYL-19-KETO-PG COMPOUNDS

[75] Inventor: John C. Sih, Kalamazoo, Mich.

[73] Assignee: The Upjohn Company, Kalamazoo, Mich.

[21] Appl. No.: 132,349

[22] Filed: Mar. 20, 1980

Related U.S. Application Data

[62] Division of Ser. No. 25,879, Apr. 2, 1980.

[51] Int. Cl.³ ............................................. C07C 177/00
[52] U.S. Cl. .................................. 568/330; 568/379; 568/380
[58] Field of Search ........................ 568/330, 379, 380

[56] References Cited

PUBLICATIONS

Sih, JACS, vol. 91, 3685 (1969).

*Primary Examiner*—Paul J. Killos
*Attorney, Agent, or Firm*—Robert A. Armitage

[57] ABSTRACT

The present invention provides novel 2-decarboxy-2-hydroxymethyl-19-keto-PG compounds, which are useful for a variety of pharmacological purposes, e.g., antiasthmatic indications.

262 Claims, No Drawings

2-DECARBOXY-2-HYDROXYMETHYL-19-KETO-PG COMPOUNDS

DESCRIPTION

CROSS REFERENCE TO RELATED APPLICATION

This application is a division of Ser. No. 025,879, filed Apr. 2, 1979, now pending.

BACKGROUND OF THE INVENTION

The present invention relates to novel prostaglandin analogs. Particularly, the invention relates to prostaglandin analogs wherein the C-19 position is substituted by oxo, i.e., 19-keto-PG compounds or 19-oxo-PG compounds. Most particularly, the present invention relates to novel 2-decarboxy-2-hydroxymethyl-19-keto-PGF compounds, a disclosure of the preparation and pharmacological use of which is incorporated here by reference from U.S. Ser. No. 025,899, filed Apr. 2, 1979, now U.S. Pat. No. 4,228,104 issued Oct. 14, 1980.

PRIOR ART

Prostaglandins exhibiting a variety of substitution at the C-19 position are known. See particularly J. C. Sih, et al., JACS 91:3685 (1969) wherein 19-oxo-PGE$_2$ and 13,14-dihydro-19-oxo-PGE$_1$ are disclosed. Further, Chemical Abstracts 86:43265H purportedly discloses 19-oxo-PGF$_2\alpha$. The abstract is derived from Japanese Kokai 76 82,245.

SUMMARY OF THE INVENTION

The present invention particularly provides: a compound of the formula

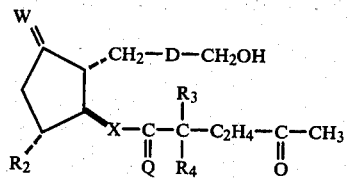

wherein D is
(1) cis-CH=CH-CH$_2$-(CH$_2$)$_g$-CH$_2$-,
(2) cis-CH=CH-CH$_2$-(CH$_2$)$_g$-CF$_2$-,
(3) cis-CH$_2$-CH=CH-CH$_2$-CH$_2$-,
(4) trans-(CH$_2$)$_3$-CH=CH-,
(5) -(CH$_2$)$_3$-(CH$_2$)$_g$-CH$_2$-,
(6) -(CH$_2$)$_3$-CH$_2$-CF$_2$-,
(7) -(CH$_2$)$_3$-O-CH$_2$-,
(8) -(CH$_2$)-O-(CH$_2$)$_2$-,
(9) -CH$_2$-O-(CH$_2$)$_3$-,
(10) -(m-Ph)-(CH$_2$)$_2$-, or
(11) -(m-Ph)-O-CH$_2$-,
wherein -(m-Ph)- is inter-meta-phenylene and
wherein g is zero, one, two, or three;
wherein Q is $\alpha$-OH:$\beta$-R$_5$ or $\alpha$-R$_5$:$\beta$-OH, wherein R$_5$ is hydrogen or methyl;
wherein R$_2$ is hydrogen, hydroxyl, or hydroxymethyl,
wherein R$_3$ and R$_4$ are hydrogen, methyl, or fluoro, being the same or different, with the proviso that one of R$_3$ and R$_4$ is fluoro only when the other is hydrogen or fluoro; and
wherein W is oxo, methylene, $\alpha$-OH:$\beta$-H, or $\alpha$-H:$\beta$-OH; and wherein X is cis- or trans-CH=CH-, -C≡C- or -CH$_2$CH$_2$-.

The compounds of the present invention are particularly useful for inducing prostaglandin-like biological effects, as described in U.S. Ser. No. 026,066. Uses of compounds in accordance with the present invention include, therefore, antiasthmatic indications.

DESCRIPTION OF THE PREFERRED EMBODIMENTS

The present invention particularly relates to:
2-decarboxy-2-hydroxymethyl-19-keto-PGF$_2\alpha$,
2-decarboxy-2-hydroxymethyl-11-deoxy-19-keto-PGF$_2\alpha$,
2-decarboxy-2-hydroxymethyl-11-deoxy-11$\alpha$-hydroxymethyl-19-keto-PGF$_1\alpha$,
2-decarboxy-2-hydroxymethyl-19-keto-PGF$_2\beta$,
2-decarboxy-2-hydroxymethyl-11-deoxy-19-keto-PGF$_2\beta$,
2-decarboxy-2-hydroxymethyl-11-deoxy-11$\alpha$-hydroxymethyl-19-keto-PGF$_2\beta$,
2-decarboxy-2-hydroxymethyl-19-keto-PGE$_2$,
2-decarboxy-2-hydroxymethyl-11-deoxy-19-keto-PGE$_2$,
2-decarboxy-2-hydroxymethyl-11-deoxy-11$\alpha$-hydroxymethyl-19-keto-PGE$_2$,
2-decarboxy-2-hydroxymethyl-9-deoxo-9-methylene-19-keto-PGE$_2$,
2-decarboxy-2-hydroxymethyl-9-deoxo-9-methylene-11-deoxy-19-keto-PGE$_2$,
2-decarboxy-2-hydroxymethyl-9-deoxo-9-methylene-11-deoxo-11$\alpha$-hydroxymethyl-19-keto-PGE$_2$,
2-decarboxy-2-hydroxymethyl-4,5-didehydro-19-keto-PGF$_1\alpha$,
2-decarboxy-2-hydroxymethyl-4,5-didehydro-19-keto-15(S)-15-methyl-PGF$_1\alpha$,
2-decarboxy-2-hydroxymethyl-4,5,13,14-tetradehydro-19-keto-PGF$_1\alpha$,
2-decarboxy-2-hydroxymethyl-4,5,13,14-tetradehydro-19-keto-16,16-difluoro-PGF$_1\alpha$,
2-decarboxy-2-hydroxymethyl-4,5-didehydro-19-keto-11-deoxy-PGF$_1\alpha$,
2-decarboxy-2-hydroxymethyl-4,5-didehydro-19-keto-11-deoxy-15(S)-15-methyl-PGF$_1\alpha$,
2-decarboxy-2-hydroxymethyl-4,5,13,14-tetradehydro-19-keto-11-deoxy-PGF$_1\alpha$,
2-decarboxy-2-hydroxymethyl-4,5,13,14-tetradehydro-19-keto-11-deoxy-16,16-difluoro-PGF$_1\alpha$,
2-decarboxy-2-hydroxymethyl-4,5-didehydro-19-keto-11-deoxy-11$\alpha$-hydroxymethyl-PGF$_1\alpha$,
2-decarboxy-2-hydroxymethyl-4,5-didehydro-19-keto-11-deoxy-11$\alpha$-hydroxymethyl-15(S)-15-methyl-PGF$_1\alpha$,
2-decarboxy-2-hydroxymethyl-4,5,13,14-tetradehydro-19-keto-11-deoxy-11$\alpha$-hydroxymethyl-PGF$_1\alpha$,
2-decarboxy-2-hydroxymethyl-4,5,13,14-tetradehydro-19-keto-11-deoxy-11$\alpha$-hydroxymethyl-16,16-difluoro-PGF$_1\alpha$,
2-decarboxy-2-hydroxymethyl-4,5-didehydro-19-keto-PGF$_1\beta$,
2-decarboxy-2-hydroxymethyl-4,5-didehydro-19-keto-15(S)-15-methyl-PGF$_1\beta$,
2-decarboxy-2-hydroxymethyl-4,5,13,14-tetradehydro-19-keto-PGF$_1\beta$,
2-decarboxy-2-hydroxymethyl-4,5,13,14-tetradehydro-19-keto-16,16-difluoro-PGF$_1\beta$,
2-decarboxy-2-hydroxymethyl-4,5-didehydro-19-keto-11-deoxy-PGF$_1\beta$, 2-decarboxy-2-hydroxymethyl-4,5-didehydro-19-keto-11-deoxy-15(S)-15-methyl-PGF$_1\beta$,
2-decarboxy-2-hydroxymethyl-4,5,13,14-tetradehydro-19-keto-11-deoxy-PGF$_1\beta$,
2-decarboxy-2-hydroxymethyl-4,5,13,14-tetradehydro-19-keto-11-deoxy-16,16-difluoro-PGF$_1\beta$,
2-decarboxy-2-hydroxymethyl-4,5-didehydro-19-keto-11-deoxy-11$\alpha$-hydroxymethyl-PGF$_1\beta$,
2-decarboxy-2-hydroxymethyl-4,5-didehydro-19-keto-11-deoxy-11$\alpha$-hydroxymethyl-15(S)-15-methyl-PGF$_1\beta$,
2-decarboxy-2-hydroxymethyl-4,5,13,14-tetradehydro-19-keto-11-deoxy-11$\alpha$-hydroxymethyl-PGF$_1\beta$,
2-decarboxy-2-hydroxymethyl-4,5,13,14-tetradehydro-19-keto-11-deoxy-11$\alpha$-hydroxymethyl-16,16-difluoro-PGF$_1\beta$,
2-decarboxy-2-hydroxymethyl-4,5-didehydro-19-keto-PGE$_1$,
2-decarboxy-2-hydroxymethyl-4,5-didehydro-19-keto-15(S)-15-methyl-PGE$_1$,
2-decarboxy-2-hydroxymethyl-4,5,13,14-tetradehydro-19-keto-PGE$_1$,
2-decarboxy-2-hydroxymethyl-4,5,13,14-tetradehydro-19-keto-16,16-difluoro-PGE$_1$,
2-decarboxy-2-hydroxymethyl-4,5-didehydro-19-keto-11-deoxy-PGE$_1$,
2-decarboxy-2-hydroxymethyl-4,5-didehydro-19-keto-11-deoxy-15(S)-15-methyl-PGE$_1$,
2-decarboxy-2-hydroxymethyl-4,5,13,14-tetradehydro-19-keto-11-deoxy-PGE$_1$,
2-decarboxy-2-hydroxymethyl-4,5,13,14-tetradehydro-19-keto-11-deoxy-16,16-difluoro-PGE$_1$,
2-decarboxy-2-hydroxymethyl-4,5-didehydro-19-keto-11-deoxy-11$\alpha$-hydroxymethyl-PGE$_1$,
2-decarboxy-2-hydroxymethyl-4,5-didehydro-19-keto-11-deoxy-11$\alpha$-hydroxymethyl-15(S)-15-methyl-PGE$_1$,
2-decarboxy-2-hydroxymethyl-4,5,13,14-tetradehydro-19-keto-11-deoxy-11$\alpha$-hydroxymethyl-PGE$_1$,
2-decarboxy-2-hydroxymethyl-4,5,13,14-tetradehydro-19-keto-11-deoxy-11$\alpha$-hydroxymethyl-16,16-difluoro-PGE$_1$,
2-decarboxy-2-hydroxymethyl-4,5-didehydro-19-keto-9-deoxo-9-methylene-PGE$_1$,
2-decarboxy-2-hydroxymethyl-4,5-didehydro-19-keto-9-deoxo-9-methylene-15(S)-15-methyl-PGE$_1$,
2-decarboxy-2-hydroxymethyl-4,5,13,14-tetradehydro-19-keto-9-deoxo-9-methylene-PGE$_1$,
2-decarboxy-2-hydroxymethyl-4,5,13,14-tetradehydro-19-keto-9-deoxo-9-methylene-16,16-difluoro-PGE$_1$,
2-decarboxy-2-hydroxymethyl-4,5-didehydro-19-keto-9-deoxo-9-methylene-11-deoxy-PGE$_1$,
2-decarboxy-2-hydroxymethyl-4,5-didehydro-19-keto-9-deoxo-9-methylene-15(S)-15-methyl-PGE$_1$,
2-decarboxy-2-hydroxymethyl-4,5,13,14-tetradehydro-19-keto-9-deoxo-9-methylene-11-deoxy-PGE$_1$,
2-decarboxy-2-hydroxymethyl-4,5,13,14-tetradehydro-19-keto-9-deoxo-9-methylene-11-deoxy-16,16-difluoro-PGE$_1$,
2-decarboxy-2-hydroxymethyl-4,5-didehydro-19-keto-9-deoxo-9-methylene-11-deoxy-11$\alpha$-hydroxymethyl-PGE$_1$,
2-decarboxy-2-hydroxymethyl-4,5-didehydro-19-keto-9-deoxo-9-methylene-11-deoxy-11$\alpha$-hydroxymethyl-15(S)-15-methyl-PGE$_1$,
2-decarboxy-2-hydroxymethyl-4,5,13,14-tetradehydro-19-keto-9-deoxo-9-methylene-11-deoxy-11$\alpha$-hydroxymethyl-PGE$_1$,
2-decarboxy-2-hydroxymethyl-4,5,13,14-tetradehydro-19-keto-9-deoxo-9-methylene-11-deoxy-11$\alpha$-hydroxymethyl-16,16-difluoro-PGE$_1$,
2-decarboxy-2-hydroxymethyl-2,3-didehydro-19-keto-PGF$_1\alpha$,
2-decarboxy-2-hydroxymethyl-2,3-didehydro-19-keto-16,16-difluoro-PGF$_1\alpha$,
2-decarboxy-2-hydroxymethyl-2,3-didehydro-19-keto-15(S)-15-methyl-PGF$_1\alpha$,
2-decarboxy-2-hydroxymethyl-2,3-didehydro-19-keto-11-deoxy-PGF$_1\alpha$,
2-decarboxy-2-hydroxymethyl-2,3-didehydro-19-keto-11-deoxy-16,16-difluoro-PGF$_1\alpha$,
2-decarboxy-2-hydroxymethyl-2,3-didehydro-19-keto-11-deoxy-15(S)-15-methyl-PGF$_1\alpha$,
2-decarboxy-2-hydroxymethyl-2,3-didehydro-19-keto-11-deoxy-11$\alpha$-hydroxymethyl-PGF$_1\alpha$,
2-decarboxy-2-hydroxymethyl-2,3-didehydro-19-keto-11-deoxy-11$\alpha$-hydroxymethyl-16,16-difluoro-PGF$_1\alpha$,
2-decarboxy-2-hydroxymethyl-2,3-didehydro-19-keto-11-deoxy-11$\alpha$-hydroxymethyl-15(S)-15-methyl-PGF$_1\alpha$,
2-decarboxy-2-hydroxymethyl-2,3-didehydro-19-keto-PGF$_1\beta$,
2-decarboxy-2-hydroxymethyl-2,3-didehydro-19-keto-16,16-difluoro-PGF$_1\beta$,
2-decarboxy-2-hydroxymethyl-2,3-didehydro-19-keto-15(S)-15-methyl-PGF$_1\beta$,
2-decarboxy-2-hydroxymethyl-2,3-didehydro-19-keto-11-deoxy-PGF$_1\beta$,
2-decarboxy-2-hydroxymethyl-2,3-didehydro-19-keto-11-deoxy-16,16-difluoro-PGF$_1\beta$,
2-decarboxy-2-hydroxymethyl-2,3-didehydro-19-keto-11-deoxy-15(S)-15-methyl-PGF$_1\beta$,
2-decarboxy-2-hydroxymethyl-2,3-didehydro-19-keto-PGE$_1$,
2-decarboxy-2-hydroxymethyl-2,3-didehydro-19-keto-16,16-difluoro-PGE$_1$,
2-decarboxy-2-hydroxymethyl-2,3-didehydro-19-keto-15(S)-15-methyl-PGE$_1$,
2-decarboxy-2-hydroxymethyl-2,3-didehydro-19-keto-11-deoxy-PGE$_1$,
2-decarboxy-2-hydroxymethyl-2,3-didehydro-19-keto-11-deoxy-16,16-difluoro-PGE$_1$,
2-decarboxy-2-hydroxymethyl-2,3-didehydro-19-keto-11-deoxy-15(S)-15-methyl-PGE$_1$,
2-decarboxy-2-hydroxymethyl-2,3-didehydro-19-keto-11-deoxy-11$\alpha$-hydroxymethyl-PGE$_1$,
2-decarboxy-2-hydroxymethyl-2,3-didehydro-19-keto-11-deoxy-11$\alpha$-hydroxymethyl-16,16-difluoro-PGE$_1$,
2-decarboxy-2-hydroxymethyl-2,3-didehydro-19-keto-11-deoxy-11$\alpha$-hydroxymethyl-15(S)-15-methyl-PGE$_1$,
2-decarboxy-2-hydroxymethyl-2,3-didehydro-19-keto-9-deoxo-9-methylene-PGE$_1$,
2-decarboxy-2-hydroxymethyl-2,3-didehydro-19-keto-9-deoxo-9-methylene-16,16-difluoro-PGE$_1$,
2-decarboxy-2-hydroxymethyl-2,3-didehydro-19-keto-9-deoxo-9-methylene-15(S)-15-methyl-PGE$_1$,
2-decarboxy-2-hydroxymethyl-2,3-didehydro-19-keto-9-deoxo-9-methylene-11-deoxy-PGE$_1$,
2-decarboxy-2-hydroxymethyl-2,3-didehydro-19-keto-9-deoxo-9-methylene-11-deoxy-16,16-difluoro-PGE$_1$,
2-decarboxy-2-hydroxymethyl-2,3-didehydro-19-keto-9-deoxo-9-methylene-11-deoxy-15(S)-15-methyl-PGE$_1$, 2-decarboxy-2-hydroxymethyl-2,3-didehydro-19-keto-9-deoxo-9-methylene-11-deoxy-11α-hydroxymethyl-PGE$_1$, 2-decarboxy-2-hydroxymethyl-2,3-didehydro-19-keto-9-deoxo-9-methylene-11-deoxy-11α-hydroxymethyl-16,16-difluoro-PGE$_1$, 2-decarboxy-2-hydroxymethyl-2,3-didehydro-19-keto-9-deoxo-9-methylene-11-deoxy-11α-hydroxymethyl-15(S)-15-methyl-PGE$_1$, 2-decarboxy-2-hydroxymethyl-19-keto-PGF$_{1\alpha}$, 2-decarboxy-2-hydroxymethyl-16,16-dimethyl-19-keto-PGF$_{1\alpha}$, 2-decarboxy-2-hydroxymethyl-16,16-difluoro-19-keto-PGF$_{1\alpha}$, 2-decarboxy-2-hydroxymethyl-13,14-dihydro-19-keto-PGF$_{1\alpha}$, 2-decarboxy-2-hydroxymethyl-11-deoxy-19-keto-PGF$_{1\alpha}$, 2-decarboxy-2-hydroxymethyl-11-deoxy-16,16-dimethyl-19-keto-PGF$_{1\alpha}$, 2-decarboxy-2-hydroxymethyl-11-deoxy-16,16-difluoro-19-keto-PGF$_{1\alpha}$, 2-decarboxy-2-hydroxymethyl-11-deoxy-13,14-dihydro-19-keto-PGF$_{1\alpha}$, 2-decarboxy-2-hydroxymethyl-11-deoxy-11α-hydroxymethyl-19-keto-PGF$_{1\alpha}$, 2-decarboxy-2-hydroxymethyl-11-deoxy-11α-hydroxymethyl-16,16-dimethyl-19-keto-PGF$_{1\alpha}$, 2-decarboxy-2-hydroxymethyl-11-deoxy-11α-hydroxymethyl-16,16-difluoro-19-keto-PGF$_{1\alpha}$, 2-decarboxy-2-hydroxymethyl-11-deoxy-11α-hydroxymethyl-13,14-dihydro-19-keto-PGF$_{1\alpha}$, 2-decarboxy-2-hydroxymethyl-19-keto-PGF$_{1\beta}$, 2-decarboxy-2-hydroxymethyl-16,16-dimethyl-19-keto-PGF$_{1\beta}$, 2-decarboxy-2-hydroxymethyl-16,16-difluoro-19-keto-PGF$_{1\beta}$, 2-decarboxy-2-hydroxymethyl-13,14-dihydro-19-keto-PGF$_{2\beta}$, 2-decarboxy-2-hydroxymethyl-11-deoxy-19-ket-PGF$_{1\beta}$, 2-decarboxy-2-hydroxymethyl-11-deoxy-16,16-dimethyl-19-keto-PGF$_{1\beta}$, 2-decarboxy-2-hydroxymethyl-11-deoxy-16,16-difluoro-19-keto-PGF$_{1\beta}$, 2-decarboxy-2-hydroxymethyl-11-deoxy-13,14-dihydro-19-keto-PGF$_{1\beta}$, 2-decarboxy-2-hydroxymethyl-11-deoxy-11α-hydroxymethyl-19-keto-PGF$_{1\beta}$, 2-decarboxy-2-hydroxymethyl-11-deoxy-11α-hydroxymethyl-16,16-dimethyl-19-keto-PGF$_{1\beta}$, 2-decarboxy-2-hydroxymethyl-11-deoxy-11α-hydroxymethyl-16,16-difluoro-19-keto-PGF$_{1\beta}$, 2-decarboxy-2-hydroxymethyl-11-deoxy-11α-hydroxymethyl-13,14-dihydro-19-keto-PGF$_{1\beta}$, 2-decarboxy-2-hydroxymethyl-19-keto-PGE$_1$, 2-decarboxy-2-hydroxymethyl-16,16-dimethyl-19-keto-PGE$_1$, 2-decarboxy-2-hydroxymethyl-16,16-difluoro-19-keto-PGE$_1$, 2-decarboxy-2-hydroxymethyl-13,14-dihydro-19-keto-PGE$_1$, 2-decarboxy-2-hydroxymethyl-11-deoxy-19-keto-PGE$_1$, 2-decarboxy-2-hydroxymethyl-11-deoxy-16,16-dimethyl-19-keto-PGE$_1$, 2-decarboxy-2-hydroxymethyl-11-deoxy-16,16-difluoro-19-keto-PGE$_1$, 2-decarboxy-2-hydroxymethyl-11-deoxy-13,14-dihydro-19-keto-PGE$_1$, 2-decarboxy-2-hydroxymethyl-11-deoxy-11α-hydroxyemthyl-19-keto-PGE$_1$, 2-decarboxy-2-hydroxymethyl-11-deoxy-11α-hydroxymethyl-16,16-dimethyl-19-keto-PGE$_1$, 2-decarboxy-2-hydroxymethyl-11-deoxy-11α-hydroxymethyl-16,16-difluoro-19-keto-PGE$_1$, 2-decarboxy-2-hydroxymethyl-11-deoxy-11α-hydroxymethyl-13,14-dihydro-19-keto-PGE$_1$, 2-decarboxy-2-hydroxymethyl-9-deoxo-9-methylene-19-keto-PGE$_1$, 2-decarboxy-2-hydroxymethyl-9-deoxo-9-methylene-16,16-dimethyl-19-keto-PGE$_1$, 2-decarboxy-2-hydroxymethyl-9-deoxo-9-methylene-16,16-difluoro-19-keto-PGE$_1$, 2-decarboxy-2-hydroxymethyl-9-deoxo-9-methylene-13,14-dihydro-19-keto-PGE$_1$, 2-decarboxy-2-hydroxymethyl-9-deoxo-9-methylene-11-deoxy-19-keto-PGE$_1$, 2-decarboxy-2-hydroxymethyl-9-deoxo-9-methylene-11-deoxy-16,16-dimethyl-19-keto-PGE$_1$, 2-decarboxy-2-hydroxymethyl-9-deoxo-9-methylene-11-deoxy-16,16-difluoro-19-keto-PGE$_1$, 2-decarboxy-2-hydroxymethyl-9-deoxo-9-methylene-11-deoxy-13,14-dihydro-19-keto-PGE$_1$, 2-decarboxy-2-hydroxymethyl-9-deoxo-9-methylene-11-deoxy-11α-hydroxymethyl-19-keto-PGE$_1$, 2-decarboxy-2-hydroxymethyl-9-deoxo-9-methylene-11-deoxy-11α-hydroxymethyl-16,16-dimethyl-19-keto-PGE$_1$, 2-decarboxy-2-hydroxymethyl-9-deoxo-9-methylene-11-deoxy-11α-hydroxymethyl-16,16-difluoro-19-keto-PGE$_1$, and 2-decarboxy-2-hydroxymethyl-9-deoxo-9-methylene-11-deoxy-11α-hydroxymethyl-13,14-dihydro-19-keto-PGE$_1$.

I claim:

1. A compound of the formula

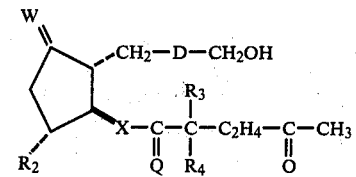

wherein D is
(1) cis-CH=CH-CH$_2$-(CH$_2$)$_g$-CH$_2$-,
(2) cis-CH=CH-CH$_2$-(CH$_2$)$_g$-CF$_2$-,
(3) cis-CH$_2$-CH=CH-CH$_2$-CH$_2$-,
(4) trans-(CH$_2$)$_3$-CH=CH-,
(5) -(CH$_2$)$_3$-(CH$_2$)$_g$-CH$_2$-,
(6) -(CH$_2$)$_3$-CH$_2$-CF$_2$-,
(7) -(CH$_2$)$_3$-O-CH$_2$-,
(8) -(CH$_2$)-O-(CH$_2$)$_2$-,
(9) -CH$_2$-O-(CH$_2$)$_3$-,
(10) -(m-Ph)-(CH$_2$)$_2$-, or
(11) -(m-Ph)-O-CH$_2$-,
wherein -(m-Ph)- is inter-meta-phenylene and
wherein g is zero, one, two, or three;
wherein Q is α-OH:β-R$_5$ or α-R$_5$:β-OH, wherein R$_5$ is hydrogen or methyl;
wherein R$_2$ is hydrogen, hydroxyl, or hydroxymethyl,
wherein R$_3$ and R$_4$ are hydrogen, methyl, or fluoro, being the same or different, with the proviso that one of $R_3$ and $R_4$ is fluoro only when the other is hydrogen or fluoro; and wherein W is oxo, methylene, $\alpha$-OH:$\beta$-H, or $\alpha$-H:$\beta$-OH; and wherein X is cis- or trans-CH=CH-, -C≡C- or -CH$_2$CH-.

2. A compound according to claim 1, wherein D is cis-CH=CH-CH$_2$-(CH$_2$)$_g$-CH$_2$-.

3. A compound according to claim 2, wherein W is $\alpha$-OH:$\beta$-H.

4. A compound according to claim 3, wherein $R_2$ is hydroxyl and X is trans-CH=CH-.

5. 2-Decarboxy-2-hydroxymethyl-19-keto-PGF$_{2\alpha}$, a compound according to claim 4.

6. A compound according to claim 3, wherein $R_2$ is hydrogen and X is trans-CH=CH-.

7. 2-Decarboxy-3-hydroxymethyl-11-deoxy-19-keto-PGF$_{2\alpha}$, a compound according to claim 6.

8. A compound according to claim 3, wherein $R_2$ is hydroxymethyl and X is trans-CH=CH-.

9. 2-Decarboxy-2-hydroxymethyl-11-deoxy-11$\alpha$-hydroxymethyl-19-keto-PGF$_{2\alpha}$, a compound according to claim 8.

10. A compound according to claim 2, wherein W is $\alpha$-OH:$\beta$-H.

11. A compound according to claim 10, wherein $R_2$ is hydroxyl and X is trans-CH=CH-.

12. 2-Decarboxy-2-hydroxymethyl-19-keto-PGF$_{2\alpha}$, a compound according to claim 11.

13. A compound according to claim 10, wherein $R_2$ is hydroxyl and X is trans-CH=CH-.

14. 2-Decarboxy-2-hydroxymethyl-11-deoxy-19-keto-PGF$_{2\beta}$, a compound according to claim 13.

15. A compound according to claim 10, wherein $R_2$ is hydroxymethyl and X is trans-CH=CH-.

16. 2-Decarboxy-2-hydroxymethyl-11-deoxy-11$\alpha$-hydroxymethyl-19-keto-PGF$_{2\beta}$, a compound according to claim 15.

17. A compound according to claim 2, wherein W is oxo.

18. A compound according to claim 17, wherein $R_2$ is hydroxyl and X is trans-CH=CH-.

19. 2-Decarboxy-2-hydroxymethyl-19-keto-PGE$_2$, a compound according to claim 18.

20. A compound according to claim 17, wherein $R_2$ is hydrogen and X is trans-CH=CH-.

21. 2-Decarboxy-2-hydroxymethyl-11-deoxy-19-keto-PGE$_2$, a compound according to claim 20.

22. A compound according to claim 17, wherein $R_2$ is hydroxymethyl and X is trans-CH=CH-.

23. 2-Decarboxy-2-hydroxymethyl-11-deoxy-11$\alpha$-hydroxymethyl-19-keto-PGE$_2$, a compound according to claim 22.

24. A compound according to claim 2, wherein W is methylene.

25. A compound according to claim 24, wherein $R_2$ is hydroxyl and X is trans-CH=CH-.

26. 2-Decarboxy-2-hydroxymethyl-9-deoxo-9-methylene-19-keto-PGE$_2$, a compound according to claim 25.

27. A compound according to claim 24, wherein $R_2$ is hydrogen and X is trans-CH=CH-.

28. 2-Decarboxy-2-hydroxymethyl-9-deoxo-9-methylene-11-deoxy-19-keto-PGE$_2$, a compound according to claim 27.

29. A compound according to claim 24, wherein $R_2$ is hydroxymethyl and X is trans-CH=CH-.

30. 2-Decarboxy-2-hydroxymethyl-9-deoxo-9-methylene-11-deoxy-11$\alpha$-hydroxymethyl-19-keto-PGE$_2$, a compound according to claim 29.

31. A compound according to claim 1, wherein D is cis-CH$_2$-CH=CH-CH$_2$-CH$_2$-.

32. A compound according to claim 31, wherein W is $\beta$-OH:$\alpha$-H.

33. A compound according to claim 32, wherein $R_2$ is hydroxyl.

34. A compound according to claim 33, wherein X is trans-CH=CH-.

35. 2-Decarboxy-2-hydroxymethyl-4,5-didehydro-19-keto-PGF$_{1\alpha}$, a compound according to claim 34.

36. 2-Decarboxy-2-hydroxymethyl-4,5-didehydro-19-keto-15(S)-15-methyl-PGF$_{1\alpha}$, a compound according to claim 34.

37. A compound according to claim 33, wherein X is -C≡C-.

38. 2-Decarboxy-2-hydroxymethyl-4,5,13,14-tetradehydro-19-keto-PGF$_{1\alpha}$, a compound according to claim 37.

39. 2-Decarboxy-2-hydroxymethyl-4,5,13,14-tetradehydro-19-keto-16,16-difluoro-PGF$_{1\alpha}$, a compound according to claim 37.

40. A compound according to claim 32, wherein $R_2$ is hydrogen.

41. A compound according to claim 40, wherein X is trans-CH=CH-.

42. 2-Decarboxy-2-hydroxymethyl-4,5-didehydro-19-keto-11-deoxy-PGF$_{1\alpha}$, a compound according to claim 41.

43. 2-Decarboxy-2-hydroxymethyl-4,5-didehydro-19-keto-11-deoxy-15(S)-15-methyl-PGF$_{1\alpha}$, a compound according to claim 41.

44. A compound according to claim 32, wherein $R_2$ is hydroxymethyl.

45. 2-Decarboxy-2-hydroxymethyl-4,5,13,14-tetradehydro-19-keto-11-deoxy-PGF$_{1\alpha}$, a compound according to claim 44.

46. 2-Decarboxy-2-hydroxymethyl-4,5,13,14-tetradehydro-19-keto-11-deoxy-16,16-difluoro-PGF$_{1\alpha}$, a compound according to claim 44.

47. A compound according to claim 32, wherein $R_2$ is hydroxymethyl.

48. A compound according to claim 47, wherein X is trans-CH=CH-.

49. 2-Decarboxy-2-hydroxymethyl-4,5-didehydro-19-keto-11-deoxy-11$\alpha$-hydroxymethyl-PGF$_{1\alpha}$, a compound according to claim 48.

50. 2-Decarboxy-2-hydroxymethyl-4,5-didehydro-19-keto-11-deoxy-11$\alpha$-hydroxymethyl-15(S)-15-methyl-PGF$_{1\alpha}$, a compound according to claim 48.

51. A compound according to claim 47, wherein X is -C≡C-.

52. 2-Decarboxy-2-hydroxymethyl-4,5,13,14-tetradehydro-19-keto-11-deoxy-11$\alpha$-hydroxymethyl-PGF$_{1\alpha}$, a compound according to claim 51.

53. 2-Decarboxy-2-hydroxymethyl-4,5,13,14-tetradehydro-19-keto-11-deoxy-11$\alpha$-hydroxymethyl-16,16-difluoro-PGF$_{1\alpha}$, a compound according to claim 51.

54. A compound according to claim 31, wherein W is $\beta$-OH:$\alpha$-H.

55. A compound according to claim 54, wherein $R_2$ is hydroxyl.

56. A compound according to claim 55, wherein X is trans-CH=CH-.

57. 2-Decarboxy-2-hydroxymethyl-4,5-didehydro-19-keto-PGF$_1\beta$, a compound according to claim 56.

58. 2-Decarboxy-2-hydroxymethyl-4,5-didehydro-19-keto-15(S)-15-methyl-PGF$_1\beta$, a compound according to claim 56.

59. A compound according to claim 55, wherein X is -C≡C-.

60. 2-Decarboxy-2-hydroxymethyl-4,5,13,14-tetradehydro-19-keto-PGF$_1\beta$, a compound according to claim 59.

61. 2-Decarboxy-2-hydroxymethyl-4,5,13,14-tetradehydro-19-keto-16,16-difluoro-PGF$_1\beta$, a compound according to claim 59.

62. A compound according to claim 54, wherein R$_2$ is hydrogen.

63. A compound according to claim 62, wherein X is trans-CH=CH-.

64. 2-Decarboxy-2-hydroxymethyl-4,5-didehydro-19-keto-11-deoxy-PGF$_1\beta$, a compound according to claim 63.

65. 2-Decarboxy-2-hydroxymethyl-4,5-didehydro-19-keto-11-deoxy-15(S)-15-methyl-PGF$_1\beta$, a compound according to claim 63.

66. A compound according to claim 62, wherein X is -C≡C-.

67. 2-Decarboxy-2-hydroxymethyl-4,5,13,14-tetradehydro-19-keto-11-deoxy-PGF$_1\beta$, a compound according to claim 66.

68. 2-Decarboxy-2-hydroxymethyl-4,5,13,14-tetradehydro-19-keto-11-deoxy-16,16-difluoro-PGF$_1\beta$, a compound according to claim 66.

69. A compound according to claim 54, wherein R$_2$ is hydroxymethyl.

70. A compound according to claim 69, wherein X is trans-CH=CH-.

71. 2-Decarboxy-2-hydroxymethyl-4,5-didehydro-19-keto-11-deoxy-11$\alpha$-hydroxymethyl-PGF$_1\beta$, a compound according to claim 70.

72. 2-Decarboxy-2-hydroxymethyl-4,5-didehydro-19-keto-11-deoxy-11$\alpha$-hydroxymethyl-15(S)-15-methyl-PGF$_1\beta$, a compound according to claim 70.

73. A compound according to claim 69, wherein X is -C≡C-.

74. 2-Decarboxy-2-hydroxymethyl-4,5,13,14-tetradehydro-19-keto-11-deoxy-11$\alpha$-hydroxymethyl-PGF$_1\beta$, a compound according to claim 73.

75. 2-Decarboxy-2-hydroxymethyl-4,5,13,14-tetradehydro-19-keto-11-deoxy-11$\alpha$-hydroxymethyl-16,16-difluoro-PGF$_1\beta$, a compound according to claim 73.

76. A compound according to claim 31, wherein W is oxo.

77. A compound according to claim 76, wherein R$_2$ is hydroxyl.

78. A compound according to claim 77, wherein X is trans-CH=CH-.

79. 2-Decarboxy-2-hydroxymethyl-4,5-didehydro-19-keto-PGE$_1$, a compound according to claim 78.

80. 2-Decarboxy-2-hydroxymethyl-4,5-didehydro-19-keto-15(S)-15-methyl-PGE$_1$, a compound according to claim 78.

81. A compound according to claim 77, wherein X is -C≡C-.

82. 2-Decarboxy-2-hydroxymethyl-4,5,13,14-tetradehydro-19-keto-PGE$_1$, a compound according to claim 81.

83. 2-Decarboxy-2-hydroxymethyl-4,5,13,14-tetradehydro-19-keto-16,16-difluoro-PGE$_1$, a compound according to claim 81.

84. A compound according to claim 76, wherein R$_2$ is hydrogen.

85. A compound according to claim 84, wherein X is trans-CH=CH-.

86. 2-Decarboxy-2-hydroxymethyl-4,5-didehydro-19-keto-11-deoxy-PGE$_1$, a compound according to claim 85.

87. 2-Decarboxy-2-hydroxymethyl-4,5-didehydro-19-keto-11-deoxy-15(S)-15-methyl-PGE$_1$, a compound according to claim 85.

88. A compound according to claim 84, wherein X is -C≡C-.

89. 2-Decarboxy-2-hydroxymethyl-4,5,13,14-tetradehydro-19-keto-11-deoxy-PGE$_1$, a compound according to claim 88.

90. 2-Decarboxy-2-hydroxymethyl-4,5,13,14-tetradehydro-19-keto-11-deoxy-16,16-difluoro-PGE$_1$, a compound according to claim 88.

91. A compound according to claim 76, wherein R$_2$ is hydroxymethyl.

92. A compound according to claim 91, wherein X is trans-CH=CH-.

93. 2-Decarboxy-2-hydroxymethyl-4,5-didehydro-19-keto-11-deoxy-11$\alpha$-hydroxymethyl-PGE$_1$, a compound according to claim 92.

94. 2-Decarboxy-2-hydroxymethyl-4,5-didehydro-19-keto-11-deoxy-11$\alpha$-hydroxymethyl-15(S)-15-methyl-PGE$_1$, a compound according to claim 92.

95. A compound according to claim 91, wherein X is -C≡C-.

96. 2-Decarboxy-2-hydroxymethyl-4,5,13,14-tetradehydro-19-keto-11-deoxy-11$\alpha$-hydroxymethyl-PGE$_1$, a compound according to claim 95.

97. 2-Decarboxy-2-hydroxymethyl-4,5,13,14-tetradehydro-19-keto-11-deoxy-11$\alpha$-hydroxymethyl-16,16-difluoro-PGE$_1$, a compound according to claim 95.

98. A compound according to claim 31, wherein W is methylene.

99. A compound according to claim 98, wherein R$_2$ is hydroxyl.

100. A compound according to claim 99, wherein X is trans-CH=CH-.

101. 2-Decarboxy-2-hydroxymethyl-4,5-didehydro-19-keto-9-deoxo-9-methylene-PGE$_1$, a compound according to claim 100.

102. 2-Decarboxy-2-hydroxymethyl-4,5-didehydro-19-keto-9-deoxo-9-methylene-15(S)-15-methyl-PGE$_1$, a compound according to claim 100.

103. A compound according to claim 99, wherein X is -C≡C-.

104. 2-Decarboxy-2-hydroxymethyl-4,5,13,14-tetradehydro-19-keto-9-deoxo-9-methylene-PGE$_1$, a compound according to claim 103.

105. 2-Decarboxy-2-hydroxymethyl-4,5,13,14-tetradehydro-19-keto-9-deoxo-9-methylene-16,16-difluoro-PGE$_1$, a compound according to claim 103.

106. A compound according to claim 98, wherein R$_2$ is hydrogen.

107. A compound according to claim 106, wherein X is trans-CH=CH-.

108. 2-Decarboxy-2-hydroxymethyl-4,5-didehydro-19-keto-9-deoxo-9-methylene-11-deoxy-PGE$_1$, a compound according to claim 107.

109. 2-Decarboxy-2-hydroxymethyl-4,5-didehydro-19-keto-9-deoxo-9-methylene-15(S)-15-methyl-PGE$_1$, a compound according to claim 107.

110. A compound according to claim 106, wherein X is -C≡C-.

111. 2-Decarboxy-2-hydroxymethyl-4,5,13,14-tetradehydro-19-keto-9-deoxo-9-methylene-11-deoxy-PGE$_1$, a compound according to claim 110.

112. 2-Decarboxy-2-hydroxymethyl-4,5,13,14-tetradehydro-19-keto-9-deoxo-9-methylene-11-deoxy-16,16-difluoro-PGE$_1$, a compound according to claim 110.

113. A compound according to claim 98, wherein R$_2$ is hydroxymethyl.

114. A compound according to claim 113, wherein X is trans-CH=CH-.

115. 2-Decarboxy-2-hydroxymethyl-4,5-didehydro-19-keto-9-deoxo-9-methylene-11-deoxy-11α-hydroxymethyl-PGE$_1$, a compound according to claim 114.

116. 2-Decarboxy-2-hydroxymethyl-4,5-didehydro-19-keto-9-deoxo-9-methylene-11-deoxy-11α-hydroxymethyl-15(S)-15-methyl-PGE$_1$, a compound according to claim 114.

117. A compound according to claim 113, wherein X is -C≡C-.

118. 2-Decarboxy-2-hydroxymethyl-4,5,13,14-tetradehydro-19-keto-9-deoxo-9-methylene-11-deoxy-11α-hydroxymethyl-PGE$_1$, a compound according to claim 117.

119. 2-Decarboxy-2-hydroxymethyl-4,5,13,14-tetradehydro-19-keto-9-deoxo-9-methylene-11-deoxy-11α-hydroxymethyl-16,16-difluoro-PGE$_1$, a compound according to claim 117.

120. A compound according to claim 1, wherein D is trans-(CH$_2$)$_3$-CH=CH-.

121. A compound according to claim 120, wherein W is α-OH:β-H.

122. A compound according to claim 121, wherein R$_2$ is hydroxyl and X is trans-CH=CH-.

123. 2-Decarboxy-2-hydroxymethyl-2,3-didehydro-19-keto-PGF$_1$α, a compound according to claim 122.

124. 2-Decarboxy-2-hydroxymethyl-2,3-didehydro-19-keto-16,16-difluoro-PGF$_1$α, a compound according to claim 122.

125. 2-Decarboxy-2-hydroxymethyl-2,3-didehydro-19-keto-15(S)-15-methyl-PGF$_1$α, a compound according to claim 122.

126. A compound according to claim 121, wherein R$_2$ is hydrogen and X is trans-CH=CH-.

127. 2-Decarboxy-2-hydroxymethyl-2,3-didehydro-19-keto-11-deoxy-PGF$_1$α, a compound according to claim 126.

128. 2-Decarboxy-2-hydroxymethyl-2,3-didehydro-19-keto-11-deoxy-16,16-difluoro-PGF$_1$α, a compound according to claim 126.

129. 2-Decarboxy-2-hydroxymethyl-2,3-didehydro-19-keto-11-deoxy-15(S)-15-methyl-PGF$_1$α, a compound according to claim 126.

130. A compound according to claim 121, wherein R$_2$ is hydroxymethyl and X is trans-CH=CH-.

131. 2-Decarboxy-2-hydroxymethyl-2,3-didehydro-19-keto-11-deoxy-11α-hydroxymethyl-PGF$_1$α, a compound according to claim 130.

132. 2-Decarboxy-2-hydroxymethyl-2,3-didehydro-19-keto-11-deoxy-11α-hydroxymethyl-16,16-difluoro-PGF$_1$α, a compound according to claim 130.

133. 2-Decarboxy-2-hydroxymethyl-2,3-didehydro-19-keto-11-deoxy-11α-hydroxymethyl-15(S)-15-methyl-PGF$_1$α, a compound according to claim 130.

134. A compound according to claim 120, wherein W is β-OH:α-H.

135. A compound according to claim 134, wherein R$_2$ is hydroxyl and X is trans-CH=C-.

136. 2-Decarboxy-2-hydroxymethyl-2,3-didehydro-19-keto-PGF$_1$β, a compound according to claim 135.

137. 2-Decarboxy-2-hydroxymethyl-2,3-didehydro-19-keto-16,16-difluoro-PGF$_1$β, a compound according to claim 135.

138. 2-Decarboxy-2-hydroxymethyl-2,3-didehydro-19-keto-15(S)-15-methyl-PGF$_1$β, a compound according to claim 135.

139. A compound according to claim 134, wherein R$_2$ is hydrogen and X is trans-CH=CH-.

140. 2-Decarboxy-2-hydroxymethyl-2,3-didehydro-19-keto-11-deoxy-PGF$_1$β, a compound according to claim 139.

141. 2-Decarboxy-2-hydroxymethyl-2,3-didehydro-19-keto-11-deoxy-16,16-difluoro-PGF$_1$β, a compound according to claim 139.

142. 2-Decarboxy-2-hydroxymethyl-2,3-didehydro-19-keto-11-deoxy-15(S)-15-methyl-PGF$_1$β, a compound according to claim 139.

143. A compound according to claim 134, wherein R$_2$ is hydroxymethyl and X is trans-CH=CH-.

144. 2-Decarboxy-2-hydroxymethyl-2,3-didehydro-19-keto-11-deoxy-11α-hydroxymethyl-PGF$_1$β, a compound according to claim 143.

145. 2-Decarboxy-2-hydroxymethyl-2,3-didehydro-19-keto-11-deoxy-11α-hydroxymethyl-16,16-difluoro-PGF$_1$β, a compound according to claim 143.

146. 2-Decarboxy-2-hydroxymethyl-2,3-didehydro-19-keto-11-deoxy-11α-hydroxymethyl-15(S)-15-methyl-PGF$_1$β, a compound according to claim 143.

147. A compound according to claim 120, wherein W is oxo.

148. A compound according to claim 147, wherein R$_2$ is hydroxyl and X is trans-CH=CH-.

149. 2-Decarboxy-2-hydroxymethyl-2,3-didehydro-19-keto-PGE$_1$, a compound according to claim 148.

150. 2-Decarboxy-2-hydroxymethyl-2,3-didehydro-19-keto-16,16-difluoro-PGE$_1$, a compound according to claim 148.

151. 2-Decarboxy-2-hydroxymethyl-2,3-didehydro-19-keto-15(S)-15-methyl-PGE$_1$, a compound according to claim 148.

152. A compound according to claim 147, wherein R$_2$ is hydrogen and X is trans-CH=CH-.

153. 2-Decarboxy-2-hydroxymethyl-2,3-didehydro-19-keto-11-deoxy-PGE$_1$, a compound according to claim 152.

154. 2-Decarboxy-2-hydroxymethyl-2,3-didehydro-19-keto-11-deoxy-16,16-difluoro-PGE$_1$, a compound according to claim 152.

155. 2-Decarboxy-2-hydroxymethyl-2,3-didehydro-19-keto-11-deoxy-15(S)-15-methyl-PGE$_1$, a compound according to claim 152.

156. A compound according to claim 147, wherein R$_2$ is hydroxymethyland X is trans-CH=CH-.

157. 2-Decarboxy-2-hydroxymethyl-2,3-didehydro-19-keto-11-deoxy-11α-hydroxymethyl-PGE$_1$, a compound according to claim 156.

158. 2-Decarboxy-2-hydroxymethyl-2,3-didehydro-19-keto-11-deoxy-11α-hydroxymethyl-16,16-difluoro-PGE$_1$, a compound according to claim 156.

159. 2-Decarboxy-2-hydroxymethyl-2,3-didehydro-19-keto-11-deoxy-11α-hydroxymethyl-15(S)-15-methyl-PGE$_1$, a compound according to claim 156.

160. A compound according to claim 120, wherein W is methylene.

161. A compound according to claim 160, wherein R$_2$ is hydroxyl and X is trans-CH=CH-.

162. 2-Decarboxy-2-hydroxymethyl-2,3-didehydro-19-keto-9-deoxo-9-methylene-PGE$_1$, a compound according to claim 161.

163. 2-Decarboxy-2-hydroxymethyl-2,3-didehydro-19-keto-9-deoxo-9-methylene-16,16-difluoro-PGE$_1$, a compound according to claim 161.

164. 2-Decarboxy-2-hydroxymethyl-2,3-didehydro-19-keto-9-deoxy-9-methylene-15(S)-15-methyl-PGE$_1$, a compound according to claim 161.

165. A compound according to claim 160, wherein R$_2$ is hydrogen and X is trans-CH=CH-.

166. 2-Decarboxy-2-hydroxymethyl-2,3-didehydro-19-keto-9-deoxo-9-methylene-11-deoxy-PGE$_1$, a compound according to claim 165.

167. 2-Decarboxy-2-hydroxymethyl-2,3-didehydro-19-keto-9-deoxo-9-methylene-11-deoxy-16,16-difluoro-PGE$_1$, a compound according to claim 165.

168. 2-Decarboxy-2-hydroxymethyl-2,3-didehydro-19-keto-9-deoxo-9-methylene-11-deoxy-15(S)-15-methyl-PGE$_1$, a compound according to claim 165.

169. A compound according to claim 160, wherein R$_2$ is hydroxymethyl and X is trans-CH=CH-.

170. 2-Decarboxy-2-hydroxymethyl-2,3-didehydro-19-keto-9-deoxo-9-methylene-11-deoxy-11α-hydroxymethyl-PGE$_1$, a compound according to claim 169.

171. 2-Decarboxy-2-hydroxymethyl-2,3-didehydro-19-keto-9-deoxo-9-methylene-11-deoxy-11α-hydroxymethyl-16,16-difluoro-PGE$_1$, a compound according to claim 169.

172. 2-Decarboxy-2-hydroxymethyl-2,3-didehydro-19-keto-9-deoxo-9-methylene-11-deoxy-11α-hydroxymethyl-15(S)-15-methyl-PGE$_1$, a compound according to claim 169.

173. A compound according to claim 1, wherein D is -(CH$_2$)$_3$-(CH$_2$)$_g$-CH$_2$-.

174. A compound according to claim 173, wherein g is one.

175. A compound according to claim 174, wherein W is α-OH:β-H.

176. A compound according to claim 175, wherein R$_2$ is hydroxyl.

177. A compound according to claim 176, wherein X is trans-CH=CH-.

178. 2-Decarboxy-2-hydroxymethyl-19-keto-PGF$_1$α, a compound according to claim 177.

179. 2-Decarboxy-2-hydroxymethyl-16,16-dimethyl-19-keto-PGF$_1$α, a compound according to claim 177.

180. 2-Decarboxy-2-hydroxymethyl-16,16-difluoro-19-keto-PGF$_1$α, a compound according to claim 177.

181. A compound according to claim 176, wherein X is -CH$_2$CH$_2$-.

182. 2-Decarboxy-2-hydroxymethyl-13,14-dihydro-19-keto-PGF$_1$α, a compound according to claim 181.

183. A compound according to claim 175, wherein R$_2$ is hydrogen.

184. A compound according to claim 183, wherein X is trans-CH=CH-.

185. 2-Decarboxy-2-hydroxymethyl-11-deoxy-19-keto-PGF$_1$α, a compound according to claim 184.

186. 2-Decarboxy-2-hydroxymethyl-11-deoxy-16,16-dimethyl-19-keto-PGF$_1$α, a compound according to claim 184.

187. 2-Decarboxy-2-hydroxymethyl-11-deoxy-16,16-difluoro-19-keto-PGF$_1$α, a compound according to claim 184.

188. A compound according to claim 183, wherein X is -CH$_2$CH$_2$-.

189. 2-Decarboxy-2-hydroxymethyl-11-deoxy-13,14-dihydro-19-keto-PGF$_1$α, a compound according to claim 188.

190. A compound according to claim 175, wherein R$_2$ is hydroxymethyl.

191. A compound according to claim 190, wherein X is trans-CH=CH-.

192. 2-Decarboxy-2-hydroxymethyl-11-deoxy-11α-hydroxymethyl-19-keto-PGF$_1$α, a compound according to claim 191.

193. 2-Decarboxy-2-hydroxymethyl-11-deoxy-11α-hydroxymethyl-16,16-dimethyl-19-keto-PGF$_1$α, a compound according to claim 191.

194. 2-Decarboxy-2-hydroxymethyl-11-deoxy-11α-hydroxymethyl-16,16-difluoro-19-keto-PGF$_1$α, a compound according to claim 191.

195. A compound according to claim 190, wherein X is -CH$_2$CH$_2$-.

196. 2-Decarboxy-2-hydroxymethyl-11-deoxy-11α-hydroxymethyl-13,14-dihydro-19-keto-PGF$_1$α, a compound according to claim 195.

197. A compound according to claim 174, wherein W is β:OH:α-H.

198. A compound according to claim 197, wherein R$_2$ is hydroxyl.

199. A compound according to claim 198, wherein X is trans-CH=CH-.

200. 2-Decarboxy-2-hydroxymethyl-19-keto-PGF$_1$α, a compound according to claim 199.

201. 2-Decarboxy-2-hydroxymethyl-19-keto-16,16-dimethyl-PGF$_1$β, a compound according to claim 199.

202. 2-Decarboxy-2-hydroxymethyl-19-keto-16,16-difluoro-PGF$_1$β, a compound according to claim 199.

203. A compound according to claim 198, wherein X is -CH$_2$CH$_2$-.

204. 2-Decarboxy-2-hydroxymethyl-13,14-dihydro-19-keto-PGF$_2$β, a compound according to claim 203.

205. A compound according to claim 197, wherein R$_2$ is hydrogen.

206. A compound according to claim 205, wherein X is trans-CH=CH-.

207. 2-Decarboxy-2-hydroxymethyl-11-deoxy-19-keto-PGF$_1$β, a compound according to claim 206.

208. 2-Decarboxy-2-hydroxymethyl-11-deoxy-16,16-dimethyl-19-keto-PGF$_1$β, a compound according to claim 206.

209. 2-Decarboxy-2-hydroxymethyl-11-deoxy-16,16-difluoro-19-keto-PGF$_1$β, a compound according to claim 206.

210. A compound according to claim 205, wherein X is -CH$_2$CH$_2$-.

211. 2-Decarboxy-2-hydroxymethyl-11-deoxy-13,14-dihydro-19-keto-PGF$_1$β, a compound according to claim 210.

212. A compound according to claim 197, wherein R$_2$ is hydroxymethyl.

213. A compound according to claim 212, wherein X is trans-CH=CH-.

214. 2-Decarboxy-2-hydroxymethyl-11-deoxy-11α-hydroxymethyl-19-keto-PGF$_1$β, a compound according to claim 213.

215. 2-Decarboxy-2-hydroxymethyl-11-deoxy-11α-hydroxymethyl-16,16-dimethyl-19-keto-PGF$_1$β, a compound according to claim 213.

216. 2-Decarboxy-2-hydroxymethyl-11-deoxy-11α-hydroxymethyl-16,16-difluoro-19-keto-PGF$_1$β, a compound according to claim 213.

217. A compound according to claim 212, wherein X is -CH$_2$CH$_2$-.

218. 2-Decarboxy-2-hydroxymethyl-11-deoxy-11α-hydroxymethyl-13,14-dihydro-19-keto-PGF$_1$β, a compound according to claim 217.

219. A compound according to claim 174, wherein W is oxo.

220. A compound according to claim 219, wherein R$_2$ is hydroxyl.

221. A compound according to claim 220, wherein X is trans-CH=CH-.

222. 2-Decarboxy-2-hydroxymethyl-19-keto-PGE$_1$, a compound according to claim 221.

223. 2-Decarboxy-2-hydroxymethyl-16,16-dimethyl-19-keto-PGE$_1$, a compound according to claim 221.

224. 2-Decarboxy-2-hydroxymethyl-16,16-difluoro-19-keto-PGE$_1$, a compound according to claim 221.

225. A compound according to claim 220, wherein X is -CH$_2$CH$_2$-.

226. 2-Decarboxy-2-hydroxymethyl-13,14-dihydro-19-keto-PGE$_1$, a compound according to claim 225.

227. A compound according to claim 219, wherein R$_2$ is hydrogen.

228. A compound according to claim 227, wherein X is trans-CH=CH-.

229. 2-Decarboxy-2-hydroxymethyl-11-deoxy-19-keto-PGE$_1$, a compound according to claim 228.

230. 2-Decarboxy-2-hydroxymethyl-11-deoxy-16,16-dimethyl-19-keto-PGE$_1$, a compound according to claim 228.

231. 2-Decarboxy-2-hydroxymethyl-11-deoxy-16,16-difluoro-19-keto-PGE$_1$, a compound according to claim 228.

232. A compound according to claim 227, wherein X is -CH$_2$CH$_2$-.

233. 2-Decarboxy-2-hydroxymethyl-11-deoxy-13,14-dihydro-19-keto-PGE$_1$, a compound according to claim 232.

234. A compound according to claim 219, wherein R$_2$ is hydroxymethyl.

235. A compound according to claim 234, wherein X is trans-CH=CH-.

236. 2-Decarboxy-2-hydroxymethyl-11-deoxy-11α-hydroxymethyl-19-keto-PGE$_1$, a compound according to claim 235.

237. 2-Decarboxy-2-hydroxymethyl-11-deoxy-11α-hydroxymethyl-16,16-dimethyl-19-keto-PGE$_1$, a compound according to claim 235.

238. 2-Decarboxy-2-hydroxymethyl-11-deoxy-11α-hydroxymethyl-16,16-difluoro-19-keto-PGE$_1$, a compound according to claim 235.

239. A compound according to claim 234, wherein X is -CH$_2$CH$_2$-.

240. 2-Decarboxy-2-hydroxymethyl-11-deoxy-11α-hydroxymethyl-13,14-dihydro-19-keto-PGE$_1$, a compound according to claim 239.

241. A compound according to claim 174, wherein W is methylene.

242. A compound according to claim 241, wherein R$_2$ is hydroxyl.

243. A compound according to claim 242, wherein X is trans-CH=CH-.

244. 2-Decarboxy-2-hydroxymethyl-9-deoxo-9-methylene-19-keto-PGE$_1$, a compound according to claim 243.

245. 2-Decarboxy-2-hydroxymethyl-9-deoxo-9-methylene-16,16-dimethyl-19-keto-PGE$_1$, a compound according to claim 243.

246. 2-Decarboxy-2-hydroxymethyl-9-deoxo-9-methylene-16,16-difluoro-19-keto-PGE$_1$, a compound according to claim 243.

247. A compound according to claim 242, wherein X is -CH$_2$CH$_2$-.

248. 2-Decarboxy-2-hydroxymethyl-9-deoxy-9-methylene-13,14-dihydro-19-keto-PGE$_1$, a compound according to claim 247.

249. A compound according to claim 241, wherein R$_2$ is hydrogen.

250. A compound according to claim 249, wherein X is trans-CH=CH-.

251. 2-Decarboxy-2-hydroxymethyl-9-deoxo-9-methylene-11-deoxy-19-keto-PGE$_1$, a compound according to claim 250.

252. 2-Decarboxy-2-hydroxymethyl-9-deoxo-9-methylene-11-deoxy-16,16-dimethyl-19-keto-PGE$_1$, a compound according to claim 250.

253. 2-Decarboxy-2-hydroxymethyl-9-deoxo-9-methylene-11-deoxy-16,16-difluoro-19-keto-PGE$_1$, a compound according to claim 250.

254. A compound according to claim 249, wherein X is -CH$_2$CH$_2$-.

255. 2-Decarboxy-2-hydroxymethyl-9-deoxo-9-methylene-11-deoxy-13,14-dihydro-19-keto-PGE$_1$, a compound according to claim 254.

256. A compound according to claim 241, wherein R$_2$ is hydroxymethyl.

257. A compound according to claim 256, wherein X is trans-CH=CH-.

258. 2-Decarboxy-2-hydroxymethyl-9-deoxo-9-methylene-11-deoxy-11α-hydroxymethyl-19-keto-PGE$_1$, a compound according to claim 257.

259. 2-Decarboxy-2-hydroxymethyl-9-deoxo-9-methylene-11-deoxy-11α-hydroxymethyl-16,16-dimethyl-19-keto-PGE$_1$, a compound according to claim 257.

260. 2-Decarboxy-2-hydroxymethyl-9-deoxo-9-methylene-11-deoxy-11α-hydroxymethyl-16,16-difluoro-19-keto-PGE$_1$, a compound according to claim 257.

261. A compound according to claim 256, wherein X is -CH$_2$CH$_2$-.

262. 2-Decarboxy-2-hydroxymethyl-9-deoxo-9-methylene-11-deoxy-11α-hydroxymethyl-13,14-dihydro-19-keto-PGE$_1$, a compound according to claim 261.

* * * * *

UNITED STATES PATENT OFFICE
CERTIFICATE OF CORRECTION

Patent No. 4,296,256    Dated  20 October 1981

Inventor(s)  John C. Sih

It is certified that error appears in the above-identified patent and that said Letters Patent are hereby corrected as shown below:

Column 1, line 53, "(8) $-(CH_2)-O-(CH_2)_2-$" should read -- (8) $-(CH_2)_2-O-(CH_2)_2-$ --;

Column 6, line 58, "(8) $-(CH_2)-O-(CH_2)_2-$" should read -- (8) $-(CH_2)_2-O-(CH_2)_2-$ --;

Column 7, line 6, "$-CH_2CH-$" should read -- $-CH_2CH_2-$ --; line 29, ")$PGF_2\alpha$" should read -- $PGF_2\beta$ --;

Column 12, line 7, "trans-CH=C-" should read -- trans-CH=CH- --;

Column 14, line 32, "$\beta:OH:\alpha-H$" should read -- $\beta-OH:\alpha-H$ --.

Signed and Sealed this

Nineteenth Day of July 1983

[SEAL]

Attest:

GERALD J. MOSSINGHOFF

Attesting Officer     Commissioner of Patents and Trademarks